United States Patent
Haigis et al.

(10) Patent No.: US 10,175,469 B2
(45) Date of Patent: Jan. 8, 2019

(54) ENDOSCOPE HAVING MOVEABLE BEAM DEFLECTING ELEMENT

(71) Applicant: Scholly Fiberoptic GmbH, Denzlingen (DE)

(72) Inventors: Harald Haigis, Elzach (DE); Axel Hofer, Endingen (DE); Herbert Bohusch, Winden (DE); Matthias Kuhn, Freiburg i. Br. (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 585 days.

(21) Appl. No.: 14/445,412

(22) Filed: Jul. 29, 2014

(65) Prior Publication Data
US 2015/0034802 A1 Feb. 5, 2015

(30) Foreign Application Priority Data
Jul. 31, 2013 (DE) .................... 20 2013 006 867 U

(51) Int. Cl.
*A61B 1/04* (2006.01)
*A61B 1/00* (2006.01)
(Continued)

(52) U.S. Cl.
CPC ...... *G02B 23/2415* (2013.01); *A61B 1/00193* (2013.01); *G02B 27/2264* (2013.01); *H01L 27/14629* (2013.01)

(58) Field of Classification Search
CPC ............ A61B 1/00163; A61B 1/00165; A61B 1/00193; A61B 1/00195; A61B 1/00197;
(Continued)

(56) References Cited

U.S. PATENT DOCUMENTS 4,862,873 A * 9/1989 Yajima ............... A61B 1/00193
348/45
5,459,605 A * 10/1995 Kempf ............... A61B 1/00165
359/462
(Continued)

FOREIGN PATENT DOCUMENTS

DE 102010053881 6/2012
JP 01112216 4/1989
WO 9703378 1/1997

*Primary Examiner* — John P Leubecker
*Assistant Examiner* — William Chou
(74) *Attorney, Agent, or Firm* — Volpe and Koenig, P.C.

(57) ABSTRACT

An endoscope is provided having a first beam path formed at least in a distal end region, a second beam path formed at the end region, which second beam path is arranged offset with respect to the first beam path for recording a stereoscopic image, and an image recording chip, which is configured for electronically recording images captured via the first beam path and the second beam path. A beam deflection device is provided having at least one deflection element arranged for displacement along a straight line adjustment travel path between a first position and a second position, and the beam deflection device, in the first position, guides an image captured using the first beam path to the image recording chip and, in the second position, guides an image captured using the second beam path to the image recording chip.

17 Claims, 4 Drawing Sheets

(51) Int. Cl.
*G02B 23/24* (2006.01)
*G02B 27/22* (2018.01)
*H01L 27/146* (2006.01)

(58) Field of Classification Search
CPC ... A61B 1/00009; A61B 1/00096; A61B 1/05; A61B 1/0005
USPC ....... 600/109, 111, 129, 160, 166, 173, 182; 348/42
See application file for complete search history.

(56) References Cited

U.S. PATENT DOCUMENTS

| | | | | |
|---|---|---|---|---|
| 5,613,936 | A | * | 3/1997 | Czarnek ............. A61B 1/00177 600/129 |
| 5,976,071 | A | * | 11/1999 | Sekiya ............... A61B 1/00193 348/45 |
| 2002/0082476 | A1 | | 6/2002 | Takahashi et al. |
| 2012/0229605 | A1 | * | 9/2012 | Pretorius ................ G02B 21/22 348/46 |
| 2013/0250061 | A1 | * | 9/2013 | Hofer ................ A61B 1/00096 348/45 |

\* cited by examiner

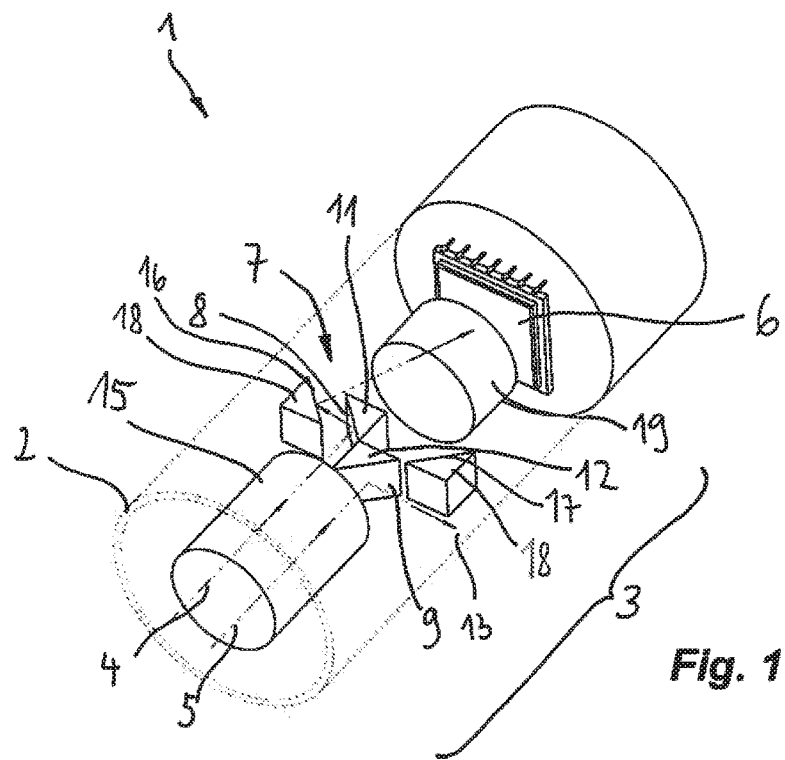
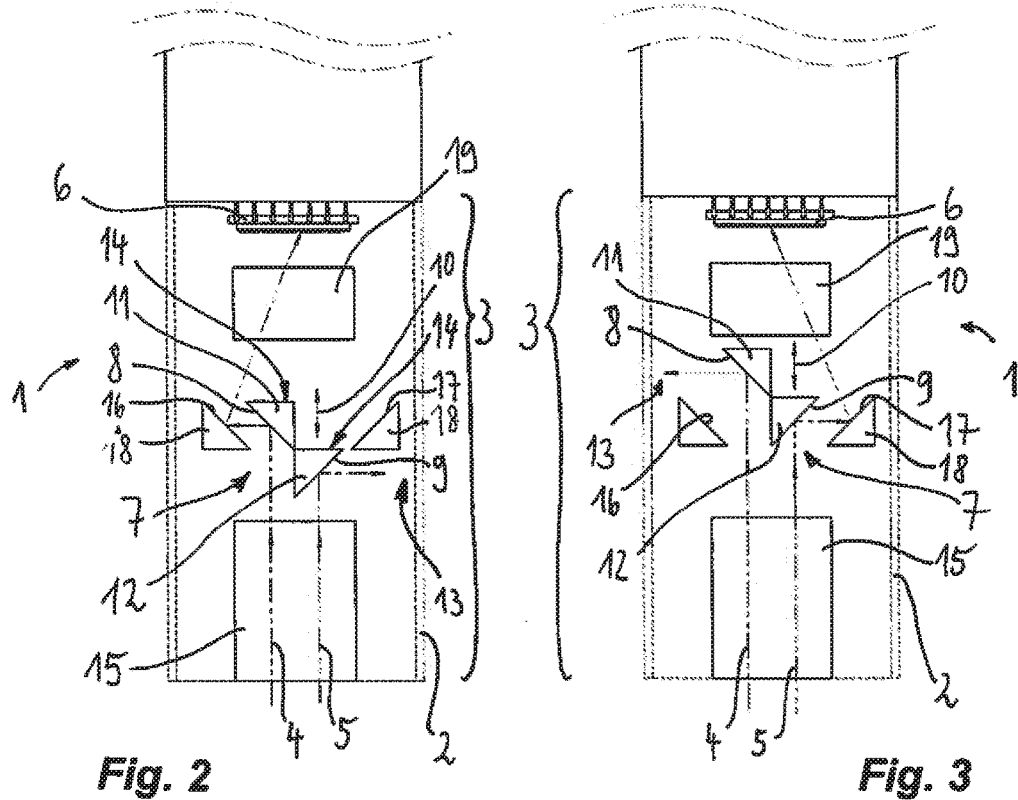
Fig. 1
Fig. 2　　　　　　　　　　　　Fig. 3

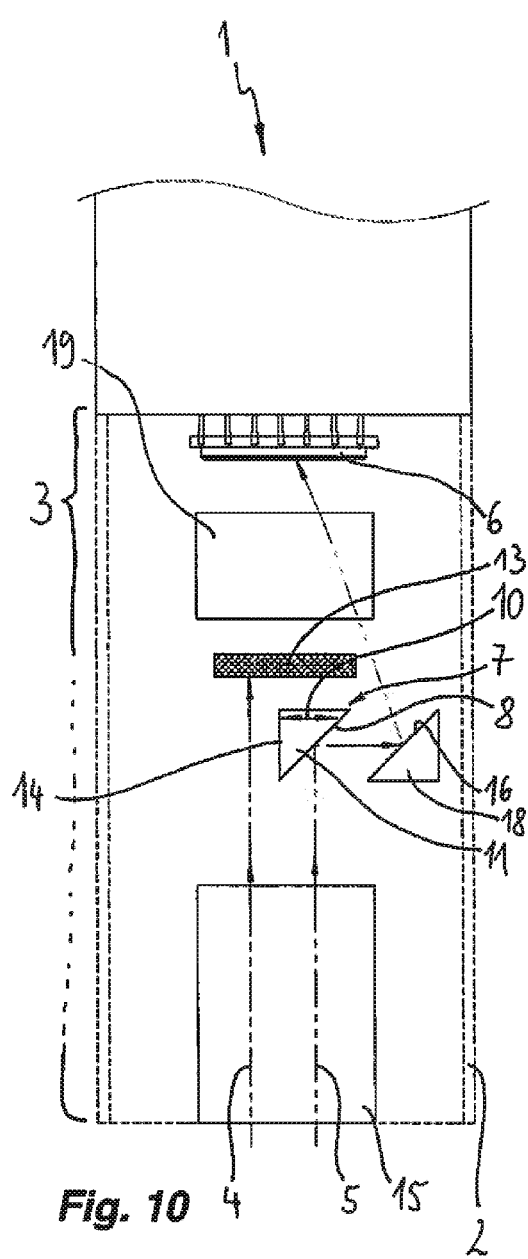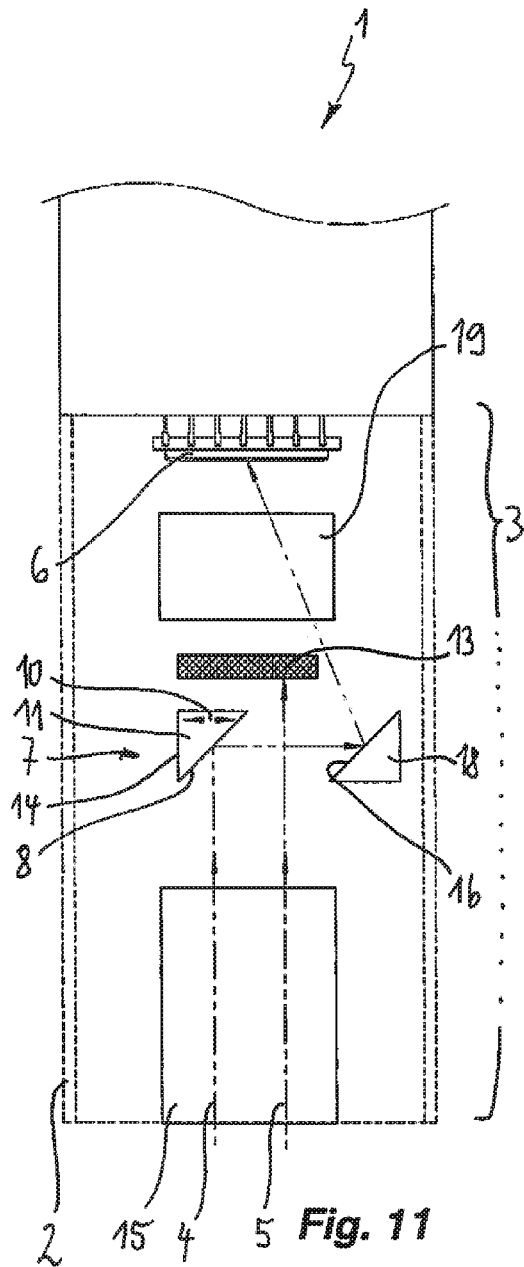

ENDOSCOPE HAVING MOVEABLE BEAM DEFLECTING ELEMENT

INCORPORATION BY REFERENCE

The following documents are incorporated herein by reference as if fully set forth: German Patent Application No. 202013006867.1, filed Jul. 31, 2013.

BACKGROUND

The invention relates to an endoscope comprising a first beam path formed at least in a distal end region, a second beam path formed at least in the end region, which second beam path is arranged offset with respect to the first beam path for recording a stereoscopic image, and comprising an image recording chip, which is configured for electronically recording images captured via the first beam path and the second beam path.

Such endoscopes are known and are used, in particular, in the medical field, but also in the non-medical field, for providing images imparting a three-dimensional impression of a cavity to be examined.

In this case, it is known to provide a pivot mirror which can be pivoted about a pivot axis, which pivot mirror can alternately guide light captured from the first beam path and from the second beam path to an image recording chip. This should render it possible to use an image recording chip, which is as large as possible and which has the highest possible image resolution, within the restricted installation space of the endoscope.

In so doing, it was found that pivoting a miniaturized mirror in the endoscope is complicated from a technological point of view.

SUMMARY

The invention is based on the object of providing an alternative embodiment of an endoscope for stereoscopic vision.

In order to achieve this object, an endoscope of the general type as set forth above is provided, in which here a beam deflection device comprising at least one deflection element that is displaceably arranged along a straight line adjustment travel path between a first position and a second position, and the beam deflection device, in the first position, guides an image captured using the first beam path to the image recording chip and, in the second position, guides an image captured using the second beam path to the image recording chip. Therefore, the adjustment travel path has at least two positions, namely the first position and the second position, and may also have further positions, for example intermediate positions. What is advantageous here is that it is possible to avoid pivot movements of the beam deflection device for alternating between the positions. The invention makes use of the discovery that linear adjustment movements are well controllable, especially in the restricted spatial conditions of an endoscope. The straight line or linear adjustment movement of the at least one deflection element of the beam deflection device therefore renders it possible to alternately supply an image captured using the first beam path and an image captured using the second beam path, for example as a right-hand image and a left-hand image, to the image recording chip. It was moreover found that linear or straight line adjustment movements are easier to generate by miniaturized components than pivot movements. Therefore, the invention offers the advantage of not requiring a conversion of a straight line drive movement into a pivot movement, but that a direct drive of the beam deflection device is made possible. This results in lower inertia of the system, as a result of which higher image refresh rates, i.e. shorter clock times for the change between the first position and the second position, can be achieved.

These high frame rates achievable by the invention render it possible to obtain stereoscopic images with a high image resolution. By way of example, this renders an HD resolution achievable.

In one embodiment of the invention, provision can be made for the at least one deflection element to be formed as a mirrored surface. What is advantageous here is that particularly light beam deflection devices can be provided.

Alternatively or additionally, provision can be made for the at least one deflection element to be formed on a prism body. What is advantageous here is that mechanically robust beam deflection devices can be provided. In the process, use can be made of total internal reflection or a mirrored surface can be formed on the prism body.

It is particularly expedient if all deflection elements of the beam deflection device are formed as mirrored surfaces and/or respectively formed on a prism body.

In one embodiment of the invention, provision can be made for at least one light trap to be formed, wherein the second beam path is guided to the at least one light trap in the first position and/or the first beam path is guided to the at least one light trap in the second position. Therefore, it is possible to avoid light from one beam path being incident on the image recording chip while an image of respectively the other beam path is intended to be recorded. What is furthermore advantageous is that a bothersome influence due to stray light on the image recording chip can be reduced.

In one embodiment of the invention, provision can be made for the beam deflection device to comprise exactly one deflection element, which is arranged in the first beam path in the first position and in the second beam path in the second position. What is advantageous here is that it is possible to create a beam deflection device with an inherent weight that is as low as possible. Therefore, the linear adjustment movement according to the invention can be carried out with little cost and with high repetition rates.

Alternatively, provision can be made for the beam deflection device to comprise a first deflection element assigned to the first beam path and a second deflection element assigned to the second beam path, wherein the first deflection element is arranged in the first beam path in the first position and the second deflection element is arranged in the second beam path in the second position. What is advantageous here is that the deflection of the beam paths for changing the image can be carried out with separate deflection elements. Therefore, short adjustment travels can be achieved, even in the case of beam paths offset far from one another.

In one embodiment of the invention, provision can be made for the first deflection element and the second deflection element to be connected or coupled to one another on the beam deflection device. What is advantageous here is that simultaneous switching of the first beam path and of the second beam path can be achieved. Therefore, it is possible to avoid dead times between an image recording of the first beam path and an image recording of the second beam path. By way of example, the first deflection element can be electrically and/or mechanically coupled to the second deflection element. Provision can also be made for the first deflection element and the second deflection element to be integrally connected to one another.

In order to achieve simultaneous switching of the first beam path and of the second beam path, provision can be made for a synchronization device to be formed, by which the first deflection element and the second deflection element can be moved synchronously. By way of example, the synchronization device can force a mechanical and/or electrical synchronization of the adjustment movements of the deflection elements.

In one embodiment of the invention, provision can be made for at least one drive element to be present, by means of which the beam deflection device can be displaced along the adjustment travel path. In this case, the drive element can be formed e.g. as a piezo-element and/or be driven or be able to be driven by electrical, magnetic and/or mechanical means. What is advantageous here is that the straight line adjustment movement can be generated electrically in a simple manner. It is further advantageous here that the vibration modes of the piezo-elements or other drive elements can be used for generating a repeating straight line adjustment movement of the deflection element or elements. Here, it is particularly expedient if each of the deflection elements has a drive element, in particular a piezo-element, by which the respective deflection element can be displaced along the adjustment travel path. By way of example, the drive elements can be coupled to one another by a synchronization device, in particular the aforementioned synchronization device, in such a way that the deflection elements can be moved synchronously and are moved synchronously.

In one embodiment of the invention, provision can be made for the image recording device to be arranged in the distal end region. What is advantageous here is that it is possible to perform a conversion of the optical image into electrical signals in the distal end region. There is no need to forward the optical signals along the endoscope. This reduces the design complexity and can increase the flexibility of the endoscope.

In one embodiment of the invention, provision can be made for the image recording chip to be arranged downstream of the beam deflection device in a direction of extent of the distal end region. What is advantageous here is that a cross section of the endoscope required by the beam paths, in particular a cross-section defined by the distance between the beam paths, can be used for the recording by the image recording chip.

In one embodiment of the invention, provision can be made for the first beam path and the second beam path to be defined by at least one common objective. What is advantageous here is that fewer individual parts are required for assembling the endoscope.

Alternatively, provision can be made for the first beam path to be defined by at least one first objective and the second beam path to be defined by at least one second objective. What is advantageous here is that simpler lens shapes can be used for the objectives.

By way of example, a plurality of objectives may be present in a beam path if different wavelengths are processed.

In one embodiment of the invention, provision can be made for the image recording chip to be aligned transverse to a direction of extent, in particular to the aforementioned direction of extent, of the distal end region. Here, transverse means that the direction of extent includes an angle that is different from zero with a surface of the image recording chip. Alternatively, transverse can be characterized in that the direction of extent is not aligned parallel to the image recording chip. It is particularly expedient if the image recording chip is aligned perpendicular to the direction of extent. What is advantageous here is that a small installation length along the direction of extent can be achieved.

In one embodiment of the invention, provision can be made for the adjustment travel path to be aligned transverse to a direction of extent, in particular to the aforementioned direction of extent, of the distal end region. What is advantageous here is that a small installation dimension of the distal end region can be achieved in the direction of extent. What is furthermore advantageous is that a cross section defined by the image recording chip can be used as space for the adjustment travel path. It is particularly expedient if the adjustment travel path is aligned perpendicular to the direction of extent.

Alternatively, provision can be made for the adjustment travel path to be aligned parallel to a direction of extent, in particular to the aforementioned direction of extent, of the distal end region. Therefore, it is possible to avoid restricting the minimum required cross-sectional area of the endoscope by the adjustment movement according to the invention, since the adjustment movement can be aligned along the direction of extent.

In one embodiment of the invention, provision can be made for the at least one deflection element to interact with at least one counter deflection element for guiding the captured image to the image recording chip. Hence, what can be achieved in a simple manner is that the image recording chip can be arranged downstream of the deflection device in the direction of extent. It is particularly expedient if the counter deflection element is arranged in the endoscope in a stationary, i.e. immobile, manner. What is advantageous here is that a structural outlay for driving the counter deflection elements can be dispensed with.

By way of example, provision can be made for the beam deflection device to have exactly one deflection element and for the deflection element to interact with the same counter deflection element both in the first position and in the second position.

In one embodiment of the invention, provision can be made for a first counter deflection element to be assigned to the first deflection element, by which counter deflection element the captured image can be deflected to the image recording device in the first position. What is particularly expedient here is if the counter deflection element is formed in a stationary manner. Therefore, a simple means for guiding the first beam path to the image recording chip and/or for switching said beam path off is created by the interaction of the deflection element with the counter deflection element.

Alternatively or additionally, provision can be made in the process for a second counter deflection element to be assigned to the second deflection element, by which counter deflection element the captured image can be guided to the image recording device in the second position. What is advantageous here is that the second beam path can be switched on and switched off for the image recording chip in an analogous fashion.

In one embodiment of the invention, provision can be made for the first counter deflection element to be arranged downstream of the beam deflection device in the first beam path and/or for the second counter element to be arranged downstream of the beam deflection device in the second beam path. Alternatively, provision can be made for the first counter deflection element to be arranged upstream of the beam deflection device in the first beam path and/or for the second counter element to be arranged upstream of the beam deflection device in the second beam path. What is advantageous here is that two alternatives are provided, by which a temporal sequence of the incidence of light on the respective deflection element and the associated counter deflection element in the respective beam paths can be predetermined.

In one embodiment of the invention, provision can be made for the first deflection element and the second deflection element to be arranged between the first counter deflection element and the second counter deflection element. What is advantageous here is that an installation space between the counter deflection elements can be used for housing the beam deflection device.

Alternatively, provision can be made for the first counter deflection element and the second counter deflection element to be arranged between the first deflection element and the second deflection element. What is advantageous here is that the stationary counter deflection elements can be arranged as close to one another as possible. It is particularly expedient if the first deflection element and the second deflection element are coupled to one another in this case by a synchronization device, in particular the aforementioned synchronization device.

In one embodiment of the invention, provision can be made for a collecting lens to be arranged between the beam deflection device and the image recording chip. What is advantageous here is that the first beam path and the second beam path can be guided by simple means to the image recording chip which can be used collectively.

What is furthermore advantageous is that the image recording chip can be used ideally by both beam paths.

BRIEF DESCRIPTION OF THE DRAWINGS

The invention will now be described in more detail on the basis of exemplary embodiments; however, it is not restricted to these exemplary embodiments. Further exemplary embodiments emerge by combining the features of individual, or a plurality of, patent claims amongst themselves and/or with the features of individual, or a plurality of, exemplary embodiments.

In the drawings:

FIG. 1 shows a much simplified three-dimensional oblique view of an endoscope according to the invention, FIG. 2 shows a side view of the endoscope in accordance with FIG. 1, comprising a beam deflection device situated in a first position, FIG. 3 shows the endoscope according to the invention in accordance with FIG. 1, comprising a beam deflection device situated in a second position, FIG. 10 shows a much simplified schematic diagram of a further endoscope according to the invention, comprising a beam deflection device situated in a second position, and FIG. 11 shows the endoscope in accordance with FIG. 10, comprising a beam deflection device situated in a first position.

DETAILED DESCRIPTION OF THE PREFERRED EMBODIMENTS

Figure 4:
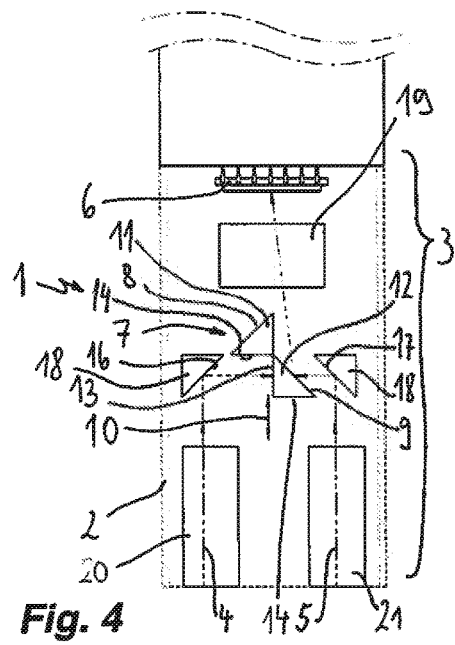
FIG. 4 shows a further endoscope according to the invention in a much simplified schematic diagram, comprising a beam deflection device situated in a second position.

For the purposes of explaining the invention, FIG. 1 shows an endoscope according to the invention, denoted as a whole by 1, in a much simplified schematic diagram. For simplifying the illustration, the endoscope wall 2 has only been indicated.

A first beam path 4 and a second beam path 5 are formed in a distal end region 3. The first beam path 4 is arranged offset with respect to the second beam path 5 in such a way that it is possible to record a stereoscopic image.

Furthermore, an image recording chip 6 is arranged in the distal end region 3, by which image recording chip images captured by the beam paths 4, 5 can be recorded.

In order to cast these images of the beam paths 4, 5 onto the image recording chip 6 in an alternating manner, a beam deflection device 7 is formed in the distal end region 3.

The beam deflection device 7 comprises a first deflection element 8 and a second deflection element 9 and is displaceably arranged along a straight line or linear adjustment travel path 10.

FIG. 2 and FIG. 3 show different states of the endoscope 1 in accordance with FIG. 1. What can be seen is that the adjustment travel path 10 is aligned parallel to the direction of extent of the distal end region 3.

FIG. 2 shows the beam deflection device 7 at one end of the adjustment travel path 10 in a first position. In this position, the beam deflection device guides an image captured using the first beam path 4 to the image recording chip 6.

FIG. 3 shows the endoscope 1 in a state in which the beam deflection device 7 has been displaced to the other end of the adjustment travel path 10 and is situated in a second position. In this second position, the beam deflection device 7 forwards an image captured using the second beam path 5 to the image recording chip 6.

Therefore, it is possible to change between the image recording chip 6 recording the first beam path 4 and recording the second beam path 5 by displacing the beam deflection device 7 between the first position and the second position, and back again.

The first deflection element 8 and the second deflection element 9 are respectively formed on prism bodies 11, 12 as a mirrored or totally internally reflecting surface.

What can be seen in FIG. 2 is that the second beam path 5 is guided to a light trap 13 in the first position. What this prevents is stray light from reaching the image recording chip 6 from the second beam path 5 when the first beam path 4 is intended to be recorded.

Analogously to this, the first beam path 4 is guided to the light trap 13 in the second position so as to keep the light thereof away from the image recording chip 6, cf. FIG. 3.

The adjustment movement along the straight line, i.e. linear, adjustment travel path 10 is carried out by electrically actuated drive elements 14, which engage on the deflection elements 8, 9. The drive elements 14 are in each case embodied as a piezo-element.

The drive elements 14 are in each case attached over an area in a manner known per se for the purposes of transmitting the adjustment movement to the deflection elements 8, 9.

What can be seen in the illustrations in accordance with FIG. 1 to FIG. 3 is that the beam deflection device 7 is arranged between the image recording chip 6 and an objective 15 used collectively by the beam paths 4, 5. Therefore, the image recording chip 6 is arranged downstream of the beam deflection device 7 in the direction of extent of the distal end region 3. What can be seen is that the image recording chip 6 is aligned transverse, in this case even perpendicular, to the direction of extent of the distal end region 3.

In order to guide the respective beam path 4, 5, switched through to the image recording chip 6, to the image recording chip 6, a first counter deflection element 16, stationary in the endoscope 1, is assigned to the first deflection element 8 and a second counter deflection element 17, likewise stationary in the endoscope 1, is assigned to the second deflection element 9.

The counter deflection elements 16 and 17 are likewise formed on prism bodies 18 as mirrored and/or totally internally reflecting surfaces.

In the first position of the beam deflection device 7 in accordance with FIG. 2, the first counter deflection element 16 therefore guides the first beam path 4 onto the image recording chip 6.

In the second position of the beam deflection device 7 in accordance with FIG. 3, the second counter deflection element 17 by contrast guides the second beam path 5 onto the image recording chip 6.

Therefore, the first deflection element 8 interacts with the first counter deflection element 16 in order, in the first position, to guide the image captured by the first beam path 4 onto the image recording chip 6. By contrast, in the second position of the beam deflection device 7, the second deflection element 9 interacts with the second counter deflection element 17 so as to guide an image captured by the second beam path 5 to the image recording chip 6.

What can be seen in FIGS. 1 to 3 is that the counter deflection elements 16, 17 are arranged downstream of the associated deflection elements 8, 9 in the respective beam path 4, 5.

In relation to the endoscope 1, the counter deflection elements 16, 17 are arranged radially outside of the deflection elements 8, 9 in such a way that the deflection elements 8, 9 are arranged between the counter deflection elements 16, 17.

A collecting lens 19 is arranged in front of the image recording chip 6 so as to collect the beam paths 4, 5 from the beam deflection device 7 and from the counter deflection elements 16, 17 on the image recording chip 6.

What can also be seen in FIGS. 1 to 3 is that the prism bodies 11, 12 are connected to one another, as a result of which a synchronization of the adjustment movements of the first deflection element 8 and of the second deflection element 9 is set up.

Figure 5:
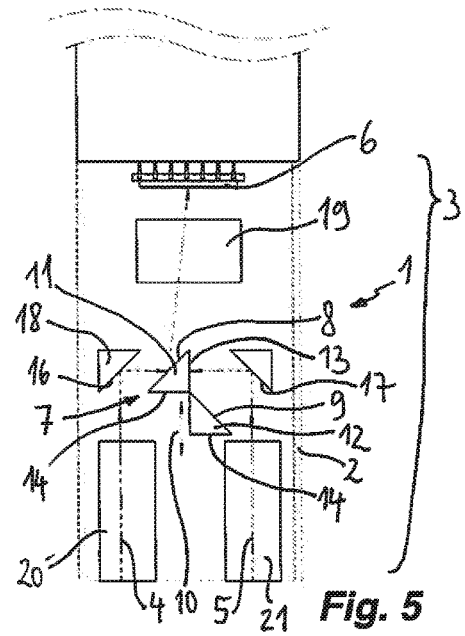
FIG. 5 shows the endoscope in accordance with FIG. 4, wherein the beam deflection device is situated in the first position.

FIG. 4 and FIG. 5 show a likewise much simplified schematic diagram of a further endoscope 1 according to the invention. Components and functional units which, in terms of function and/or design, are identical or similar to those in the exemplary embodiment in accordance with FIGS. 1 to 3 are denoted by the same reference signs and not described separately again. The explanations in respect of FIGS. 1 to 3 therefore correspondingly apply to FIGS. 4 and 5.

The exemplary embodiment in accordance with FIGS. 4 and 5 differs from the exemplary embodiment in accordance with FIGS. 1 to 3 in that the first beam path 4 is defined by a first objective 20 while the second beam path 5 is defined by a second objective 21, which is formed separately from the first objective 20.

The exemplary embodiment in accordance with FIGS. 4 and 5 further differs in that the counter deflection elements 16, 17 are arranged upstream of the associated deflection elements 8, 9 in the respective beam path 4, 5. This enables a comparatively large lateral spacing of the beam paths 4, 5 from one another to be converted into a comparatively small angle of incidence of the rays incident on the image recording chip 6.

Figure 6:
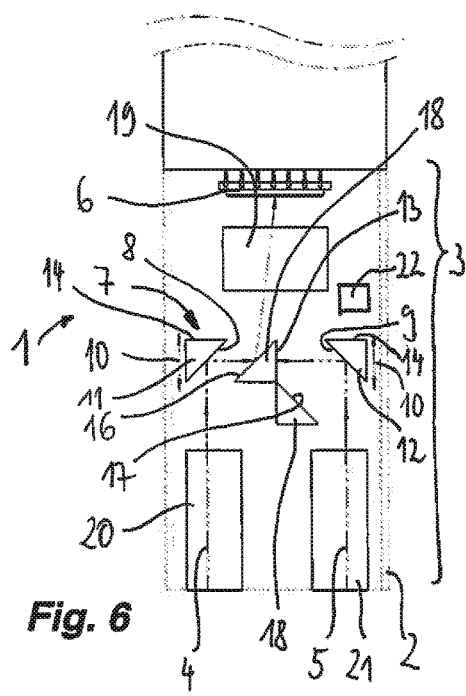
FIG. 6 shows a much simplified schematic diagram of a further endoscope according to the invention, comprising a beam deflection device situated in a first position.
Figure 7:
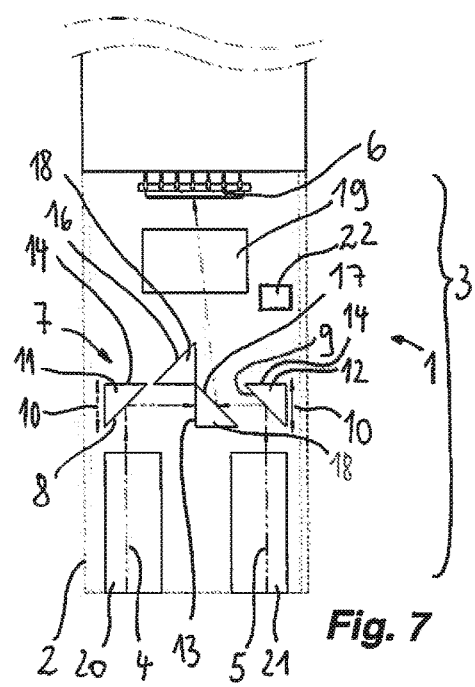
FIG. 7 shows the endoscope in accordance with FIG. 6, comprising a beam deflection device situated in a second position.

FIGS. 6 and 7 show a further exemplary embodiment according to the invention in a much simplified schematic diagram. Components and functional units which, in terms of function and/or design, are identical or similar to those in the exemplary embodiments in accordance with FIGS. 1 to 5 are denoted by the same reference signs and not described separately again. The explanations in respect of FIGS. 1 to 5 therefore correspondingly apply here.

The exemplary embodiment in accordance with FIGS. 6 and 7 differs from the exemplary embodiments in accordance with FIGS. 1 to 5 in that the prism bodies 11, 12 of the deflection elements 8, 9 are formed separate from one another or at a distance from one another.

For the purposes of synchronizing the adjustment movements, a synchronization device 22 is present. This synchronization device 22 realizes electrical and/or mechanical coupling between the deflection elements 8 and 9 or a synchronous actuation of the associated drive elements 14 so as to force a synchronous adjustment movement.

In the exemplary embodiment in accordance with FIGS. 6 and 7, the counter deflection elements 16 and 17 with the associated prism bodies 18 are arranged between the first deflection element 8 and the second deflection element 9.

The deflection elements 8, 9 are arranged upstream of the counter deflection elements 16, 17 in the respective beam path 4, 5.

The adjustment travel path 10 is once again aligned parallel to the direction of extent of the distal end region 3.

Figure 8:
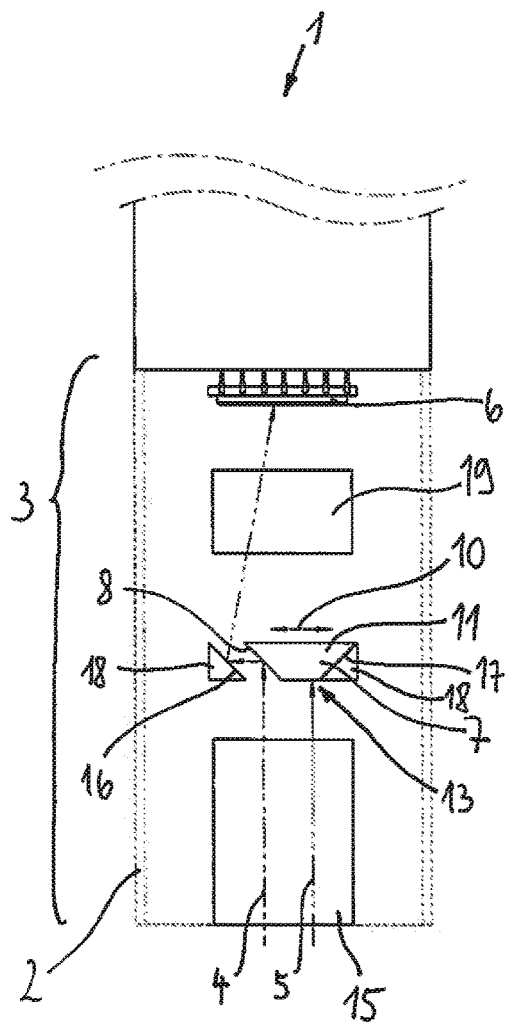
FIG. 8 shows a much simplified schematic diagram of a further endoscope according to the invention, comprising an objective which is used collectively and a beam deflection device situated in a first position.
Figure 9:
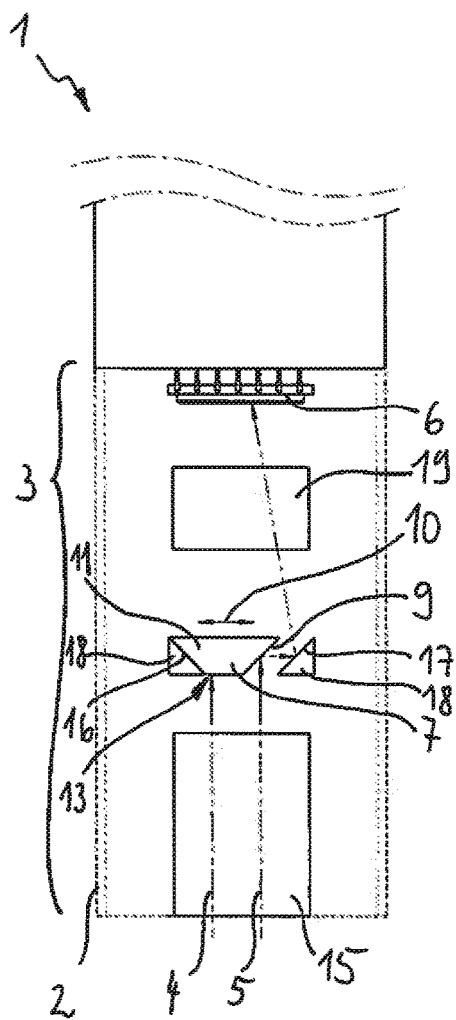
FIG. 9 shows the endoscope in accordance with FIG. 8, comprising a beam deflection device situated in a second position.

FIGS. 8 and 9 show a further exemplary embodiment of an endoscope 1 according to the invention in a much simplified schematic diagram. In FIGS. 8 and 9, components and functional units which, in terms of function and/or design, are identical or similar to those in the exemplary embodiments in accordance with FIGS. 1 to 7 are denoted by the same reference signs and not described separately. The explanations in respect of FIGS. 1 to 7 therefore correspondingly apply to FIGS. 8 and 9.

The exemplary embodiment in accordance with FIGS. 8 and 9 differs from the exemplary embodiments in accordance with FIGS. 1 to 7 in that the adjustment travel path 10 is aligned transverse, in this case even perpendicular, to the direction of extent of the distal end region 3. The adjustment movement therefore brings about a lateral deflection of the beam deflection device 7.

The first deflection device 8 and the second deflection device 9 are formed on a common prism body 11 which is displaceable by drive elements 14 (not depicted in any more detail here), for example by the aforementioned piezoelements, along the straight line adjustment travel path 10 in a manner similar to that of the remaining exemplary embodiments. In this manner, the deflection elements 8, 9 are rigidly coupled to one another in order to achieve synchronous adjustment.

What can be seen is that, in the first position in accordance with FIG. 8, the first beam path 4 is guided to the image recording chip 6 via the first deflection element 8 and the first counter deflection element 16, while the second beam path 5 is incident on a light trap 13 formed on the beam deflection device 7 and swallowed up.

Conversely, in the second position in accordance with FIG. 9, the second beam path 5 is guided to the image recording chip 6 via the second deflection element 9 and the second counter deflection element 17, while the first beam path 4 is swallowed at the light trap 13.

FIGS. 10 and 11 show, for the purposes of explaining the invention, a further exemplary embodiment of an endoscope 1 according to the invention in a much simplified schematic diagram. Components and functional units which, in terms of function and/or design, are identical or similar to those in the exemplary embodiments in accordance with FIGS. 1 to 9 are denoted by the same reference signs and not described separately. The explanations in respect of FIGS. 1 to 9 therefore correspondingly apply to FIGS. 10 and 11.

The exemplary embodiment in accordance with FIGS. 10 and 11 differs from the exemplary embodiments in accordance with FIGS. 1 to 9 in that the beam deflection device 7 comprises exactly one deflection element 8.

In the first position in accordance with FIG. 11, the deflection element 8 is arranged in the first beam path 4, while the deflection element 8 is arranged in the second beam path 5 in the second position in accordance with FIG. 10.

The respective other beam path 4, 5 is not deflected, but rather it is incident on a light trap 13 and absorbed.

In further exemplary embodiments, the individual features of the above-described exemplary embodiments are interchanged with respect to one another: thus, for example, a collectively used objective 15 can be replaced by separate objectives 20, 21, or vice versa, or a counter deflection element 16, 17 arranged downstream of the deflection element 8, 9 in the beam path 4, 5 can be arranged upstream of said deflection element by suitable pivoting of the reflection surfaces 8, 9, 16, 17, or vice versa.

Therefore, in the endoscope 1 comprising beam paths 4, 5 for stereoscopic vision, it is provided to arrange a beam deflection device 7 in the beam paths 4, 5, wherein the beam deflection device 7 can be displaced along a straight line adjustment travel path 10 between a first position and a second position in order, alternately, to guide the beam paths 4, 5 on to the image recording chip 6.

The invention claimed is:

1. An endoscope (1) comprising a first beam path (4) formed at least in a distal end region (3), a second beam path (5) formed at least in the distal end region (3), said second beam path is arranged offset with respect to the first beam path (4) for recording a stereoscopic image, an image recording chip (6) configured for electronically recording images captured via the first beam path (4) and the second beam path (5), a beam deflection device (7) comprising at least one deflection element (8, 9) formed as at least one outer mirrored surface displaceably arranged for movement along a straight line adjustment travel path (10) between a first position and a second position, at least one counter deflection element (16, 17), wherein in the first position, the at least one outer mirrored surface deflects an image captured using the first beam path (4) at a first angle to guide the image via the at least one counter deflection element (16, 17) to the image recording chip (6) and, in the second position, the at least one outer mirrored surface is linearly shifted from the first position by the beam deflection device (7) and deflects an image captured using the second beam path (5) at a second angle to guide the image via the at least one counter deflection element (16, 17) to the image recording chip (6), and at least one light trap (13), at least one of the second beam path (5) being guided to the at least one light trap (13) in the first position or the first beam path (4) being guided to the at least one light trap (13) in the second position.

2. The endoscope (1) as claimed in claim 1, wherein the beam deflection device (7) comprises exactly one deflection element (8), which is arranged in the first beam path (4) in the first position and in the second beam path (5) in the second position.

3. The endoscope (1) as claimed in claim 1, further comprising at least one drive element (14) that displaces the beam deflection device (7) along the straight line adjustment travel path (10).

4. The endoscope (1) as claimed in claim 3, wherein the at least one drive element is a piezo-element.

5. The endoscope (1) as claimed in claim 1, wherein the image recording chip (6) is arranged at least one of in the distal end region (3) or downstream of the beam deflection device (7) in a direction of extent of the distal end region (3).

6. The endoscope (1) as claimed in claim 1, wherein the first beam path (4) and the second beam path (5) are defined by at least one common objective (15).

7. The endoscope (1) as claimed in claim 1, wherein the image recording chip (6) is aligned transverse to a direction of extent of the distal end region (3) and the straight line adjustment travel path (10) is aligned transverse or parallel to the direction of extent of the distal end region (3).

8. The endoscope (1) as claimed in claim 1, wherein the at least one deflection element (8, 9) includes a first deflection element (8) assigned to the first beam path (4) and a second deflection element (9) assigned to the second beam path (5), the first deflection element (8) is arranged in the first beam path (4) in the first position and the second deflection element (9) is arranged in the second beam path (5) in the second position.

9. The endoscope (1) as claimed in claim 8, wherein the first deflection element (8) and the second deflection element (9) are connected to one another on the beam deflection device (7) or a synchronization device (22) is provided by which the first deflection element (8) and the second deflection element (9) are synchronously movable.

10. The endoscope (1) as claimed in claim 8, wherein the at least one counter deflection element (16, 17) includes a first counter deflection element (16) assigned to the first deflection element (8), said first counter deflection element guides the image captured to the image recording chip (6) in the first position, and a second counter deflection element (17) assigned to the second deflection element (9), said second counter deflection element guides the image captured to the image recording chip (6) in the second position.

11. The endoscope (1) as claimed in claim 10, wherein the first counter deflection element (16) is arranged downstream or upstream of the beam deflection device (7) in the first beam path (4) and the second counter deflection element (17) is arranged downstream or upstream of the beam deflection device (7) in the second beam path (5).

12. The endoscope (1) as claimed in claim 10, wherein the first deflection element (8) and the second deflection element (9) are arranged between the first counter deflection element (16) and the second counter deflection element (17) or wherein the first counter deflection element (16) and the second counter deflection element (17) are arranged between the first deflection element (8) and the second deflection element (9).

13. The endoscope (1) as claimed in claim 1, wherein a collecting lens (19) is arranged between the beam deflection device (7) and the image recording chip (6).

14. The endoscope (1) as claimed in claim 1, wherein the mirrored surface is on a prism body (11, 12).

15. The endoscope (1) as claimed in claim 1, wherein the at least one deflection element (8, 9) is formed on a prism body (11, 12).

16. The endoscope (1) as claimed in claim 1, wherein the first beam path (4) is defined by at least one first objective (20) and the second beam path (5) is defined by at least one second objective (21).

17. The endoscope (1) as claimed in claim 1, wherein the at least one counter deflection element (16, 17) is stationary.

* * * * *